US012771553B2

(12) United States Patent
Nguyen et al.

(10) Patent No.: US 12,771,553 B2
(45) Date of Patent: Oct. 20, 2026

(54) WIRELESS DEVICE AUTHENTICATION METHOD, SYSTEM, WEARABLE MEDICAL DEVICE, AND PRODUCT

(71) Applicants: Fasikl Incorporated, Dallas, TX (US); Hangzhou Fasikl Technology Co., Ltd, Hangzhou (CN)

(72) Inventors: Jules Anh Tuan Nguyen, Dallas, TX (US); Yangyang Hu, Hangzhou (CN); Hongzhi Yu, Hangzhou (CN); Lin Ma, Hangzhou (CN)

( * ) Notice: Subject to any disclaimer, the term of this patent is extended or adjusted under 35 U.S.C. 154(b) by 69 days.

(21) Appl. No.: 18/806,135

(22) Filed: Aug. 15, 2024

(65) Prior Publication Data

US 2024/0406000 A1 Dec. 5, 2024

(30) Foreign Application Priority Data

Jul. 26, 2024 (CN) ........................ 202411009287.4

(51) Int. Cl.
*H04L 9/32* (2006.01)
*A61N 1/36* (2006.01)
*H04W 12/106* (2021.01)

(52) U.S. Cl.
CPC ......... *H04L 9/3242* (2013.01); *H04W 12/106* (2021.01); *A61N 1/36014* (2013.01)

(58) Field of Classification Search
CPC . H04L 9/3242; H04L 9/0863; H04L 2209/80; H04L 2209/88; H04L 9/3226; H04W 12/106; H04W 12/06; H04W 12/03; A61N 1/36014; A61N 1/025; A61N 1/08; A61N 1/37254
See application file for complete search history.

(56) References Cited

U.S. PATENT DOCUMENTS 10,873,573 B2 * 12/2020 Jiang .................. H04W 12/069
12,301,727 B2 * 5/2025 Ekdahl ............. H04W 12/0471
2007/0294746 A1 12/2007 Sasakura et al.
(Continued)

OTHER PUBLICATIONS

An_authentication_protocol_for_wearable_medical_devices, IEEE (Year: 2017).*
(Continued)

*Primary Examiner* — Philip J Chea
*Assistant Examiner* — Jasmine Mochen Day
(74) *Attorney, Agent, or Firm* — Yuhao Liang

(57) ABSTRACT

Disclosed are a wireless device authentication method, a system, a wearable medical device, and a product. The wireless device authentication method includes: responding to an authentication request from the target device to generate a first encrypted packet, and sending the first encrypted packet to the target device; receiving a second encrypted packet generated by the target device by modifying the data in the first encrypted packet after verifying the decrypted first encrypted packet has passed authentication; and determining that the target device has passed authentication when the second encrypted packet meets pre-set conditions, and responding to an encrypted instruction sent by the target device. The pre-set conditions include that the keys corresponding to the second encrypted packet and the first encrypted packet are the same and the second encrypted packet has passed integrity authentication.

11 Claims, 9 Drawing Sheets

(56) References Cited

U.S. PATENT DOCUMENTS

| | | | | |
|---|---|---|---|---|
| 2015/0026783 | A1 | 1/2015 | Tseng et al. | |
| 2021/0099867 | A1 | 4/2021 | Brown et al. | |
| 2021/0184869 | A1* | 6/2021 | Trere | H04L 9/0844 |
| 2023/0171262 | A1* | 6/2023 | Pabijanskas | H04L 63/0435 713/168 |
| 2023/0208625 | A1* | 6/2023 | Wang | H04L 9/0861 713/171 |
| 2024/0056295 | A1* | 2/2024 | Marson | H04L 9/0891 |

OTHER PUBLICATIONS

Blockchain-Enabled and Data-Driven Smart Healthcare Solution for Secure and Privacy-Preserving Data Access (Year: 2022).*

* cited by examiner

WIRELESS DEVICE AUTHENTICATION METHOD, SYSTEM, WEARABLE MEDICAL DEVICE, AND PRODUCT

TECHNICAL FIELD

The present disclosure relates to the technical field of communication security, and particularly relates to a wireless device authentication method, a system, a wearable medical device, and a product.

BACKGROUND

With a rapid development of the Internet, people have increasingly raised demand for a remote control function of devices. The remote control function refers to a set of functions that enable remote control of devices through the wireless communication technology. This function is realized usually through smartphone apps or clouds, enabling users to remotely control various functions of devices without need to approach them.

Security performance of the remote control function is particularly important. When any important device data is leaked or when a device is hijacked during remote control execution, the consequences generated therefrom will be unimaginable. However, to achieve the remote control of a target device, only password authentication is required, which lacks security and cannot effectively prevent data leakage and unauthorized use of the device, thereby increasing the risk of remote control of the device.

SUMMARY

In order to overcome the defects in the prior art, the present disclosure provides a wireless device authentication method, a system, a wearable medical device, and a product to solve the problems of failure to prevent data leakage and unauthorized use of devices in the prior art, and also a high risk of remote control of the devices.

A technical solution is adopted by the present disclosure to solve the above problems: a wireless device authentication method for a device connected to a target device, including the following steps:

- responding to an authentication request from the target device to generate a first encrypted packet, and sending the first encrypted packet to the target device, where the target device includes a cloud that controls the device;
- receiving a second encrypted packet fed by the target device, where the second encrypted packet is generated by the target device by modifying the data in the first encrypted packet after verifying the decrypted first encrypted packet passes authentication; and
- when the second encrypted packet meets pre-set conditions, determining that the target device has passed authentication, and responding to an encrypted instruction sent by the target device, wherein the pre-set conditions include that the keys corresponding to the second encrypted packet and the first encrypted packet are the same and the second encrypted packet has passed integrity authentication.

Further, the step of "responding to an authentication request from the target device to generate a first encrypted packet" includes:

- receiving the authentication request from the target device to generate a random number, and using the random number and a first encryption algorithm corresponding to the key to generate the first encrypted packet.

Further, the step of "using the random number and a first encryption algorithm corresponding to the key to generate the first encrypted packet" includes:

- processing the random number using the first encryption algorithm and performing a signature operation using the key to generate a hash-based message authentication code (HMAC); and
- generating the first encrypted packet according to the HMAC of a pre-set size and the random number.

Further, the step of "generating the first encrypted packet according to the HMAC of a pre-set size and the random number" includes:

- encapsulating the HMAC of the pre-set size and the random number to form a data packet; and
- encrypting the data packet based on the key and a second encryption algorithm with a preset operating mode to obtain the first encrypted packet, where the preset operating mode includes a cipher block chaining mode.

Further, the authentication of the first encrypted packet is realized by verifying the HMAC by the target device according to the random number and the pre-stored key.

Further, the second encrypted packet that meets the preset conditions includes first data and second data, where the first data includes the random number generated after modifying in a pre-set manner, and the second data includes the HMAC corresponding to the modified random number.

Steps before the integrity authentication of the second encrypted packet include:

- decrypting the second encrypted packet using the key corresponding to the first encrypted packet to obtain the first data and the second data in the second encrypted packet; and
- obtaining the HMAC corresponding to the first data according to the first encryption algorithm and the key, and when determining that a pre-set part of the HMAC matches the second data, performing the integrity authentication of the second encrypted packet.

Further, the integrity authentication of the second encrypted packet includes:

- changing the first data according to the pre-set manner to obtain third data; and
- when determining that the third data matches the random number in the first encrypted packet, determining that the integrity authentication passes.

Based on the same inventive concept, the present disclosure further provides a wireless device authentication method for a cloud connected to a device, and the method includes the following steps:

- sending an authentication request to the device, and receiving the first encrypted packet sent by the device in response to the authentication request; and
- when determining that the decrypted first encrypted packet passes the authentication, generating the second encrypted packet based on the first encrypted packet, and feeding the second encrypted packet to the device, so that the device responds to an encrypted instruction sent by the cloud after determining that the second encrypted packet meets the pre-set conditions, where the pre-set conditions include that the keys corresponding to the second encrypted packet and the first encrypted packet are the same and the second encrypted packet has passed the integrity authentication.

Further, steps before sending the authentication request to the device include:

- when determining a first connection with the device, using a pre-set password to verify a user of the device;

when determining that the authentication fails, prompting that the current connection is illegal; and when determining that the authentication succeeds, obtaining a new password inputted by the user in a pre-set input manner, and replacing the preset password with the new password.

Further, the method further includes the following steps:

when determining that the authentication passes, generating a new key, transferring the encrypted key to the device in an encryption manner for the first encrypted packet or the second encrypted packet, and storing a configuration file of the user corresponding to the device.

Further, the method further includes the following steps:

when determining that the user satisfies the pre-set conditions and operates the device in the pre-set manner, setting the current password as the pre-set password, where the pre-set conditions include that the user has the authority of physical access to the device.

Based on the same inventive concept, the present disclosure further provides a wearable medical device, including:

a first encrypted packet generation module, configured for responding to an authentication request from the target device to generate a first encrypted packet, and sending the first encrypted packet to the target device, where the target device includes a cloud that controls the wearable medical device;

a second encrypted packet receiving module, configured for receiving a second encrypted packet fed by the target device, where the second encrypted packet is generated by the target device by modifying the data in the first encrypted packet after verifying the decrypted first encrypted packet passes authentication; and a second encrypted packet authentication module, configured for determining that the target device has passed authentication when the second encrypted packet meets pre-set conditions, and responding to an encrypted instruction sent by the target device, where the pre-set conditions include that the keys corresponding to the second encrypted packet and the first encrypted packet are the same and the second encrypted packet has passed integrity authentication.

Based on the same inventive concept, the present disclosure further provides a device authentication system, and the system includes a device and a cloud, where the cloud is in communication connection with the device, and the device authentication system implements the steps of the above method through the cloud and the device.

Based on the same inventive concept, the present disclosure further provides a computer product, including a computer program, where when the computer program is executed by the processor, the steps of any of the above methods are implemented.

Compared with the prior art, the present disclosure has the following beneficial effects: in an embodiment of the present disclosure, responding to an authentication request from the target device to generate a first encrypted packet, and sending the first encrypted packet to the target device; receiving a second encrypted packet generated by the target device by modifying the data in the first encrypted packet after verifying the decrypted first encrypted packet passes authentication; and determining that the target device has passed authentication when the second encrypted packet meets pre-set conditions, and responding to an encrypted instruction sent by the target device. The present disclosure, during communication with the target device, is capable of device authentication by means of the first encrypted packet and the second encrypted packet generated with the same key, so that only the user with the authority of physical access is allowed to control the device, thereby improving communication security, avoiding data leakage and unauthorized use of a device, and reducing the risk of remote control of the device.

DETAILED DESCRIPTIONS OF THE EMBODIMENTS

The present disclosure will be further described below with reference to the accompanying drawings and specific implementations. It should be noted that, various embodiments or technical features described below can be arbitrarily combined to form new embodiments without conflicts.

Figure 1:
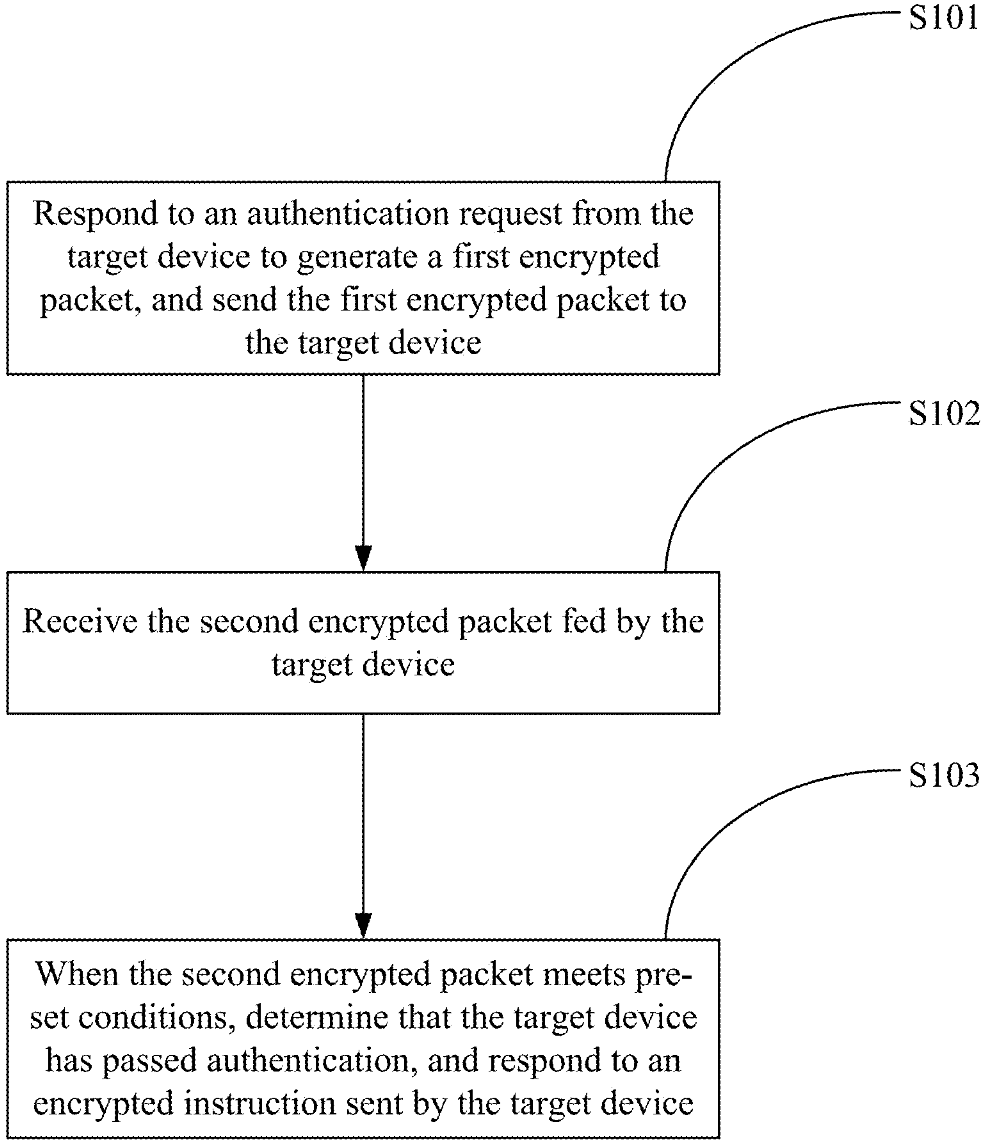
FIG. 1 is a flowchart of a wireless device authentication method in an embodiment of the present disclosure.
Figure 2:
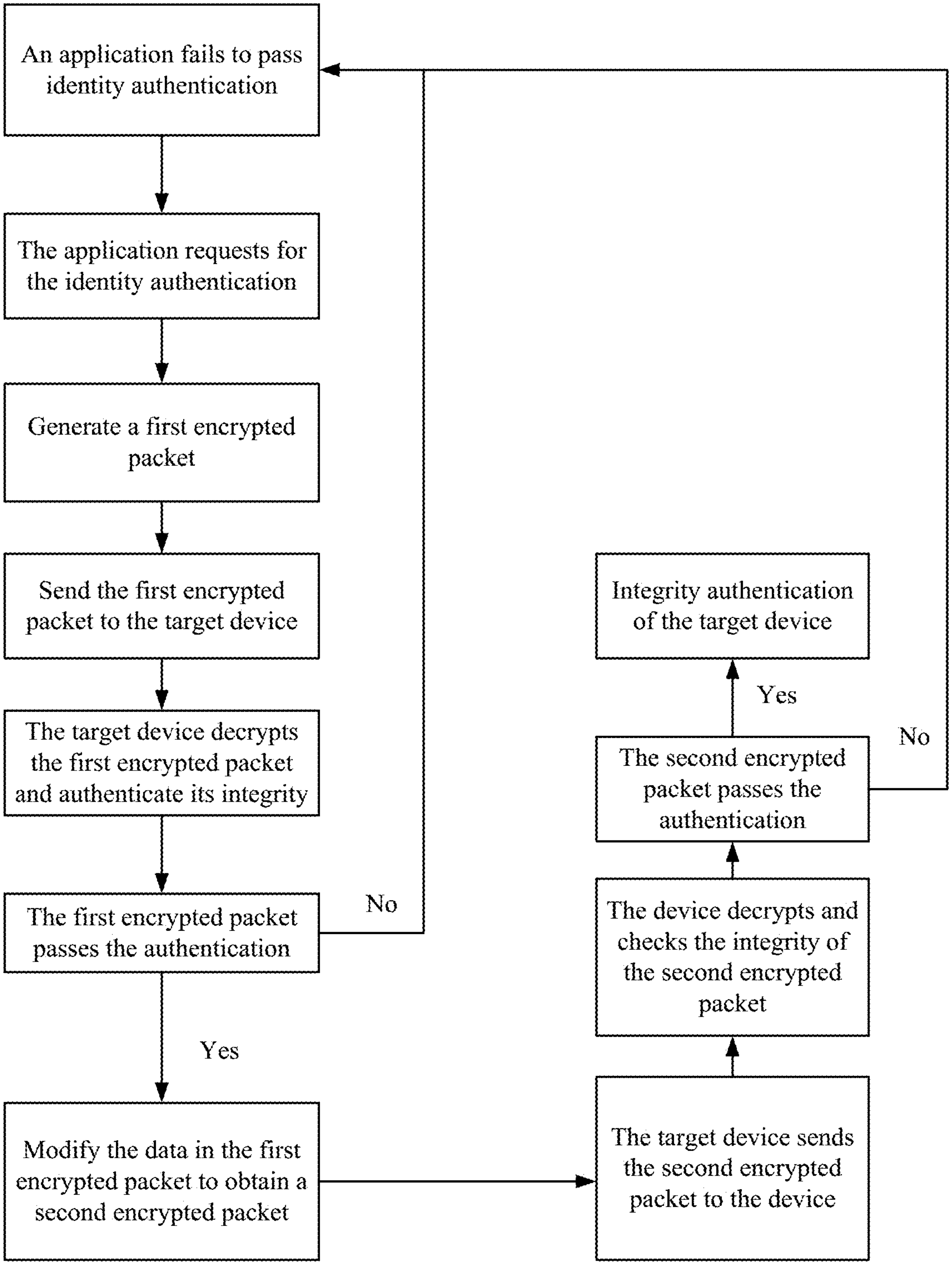
FIG. 2 is a flowchart of identity authentication according to a wireless device authentication method in an embodiment of the present disclosure.
Figure 3:
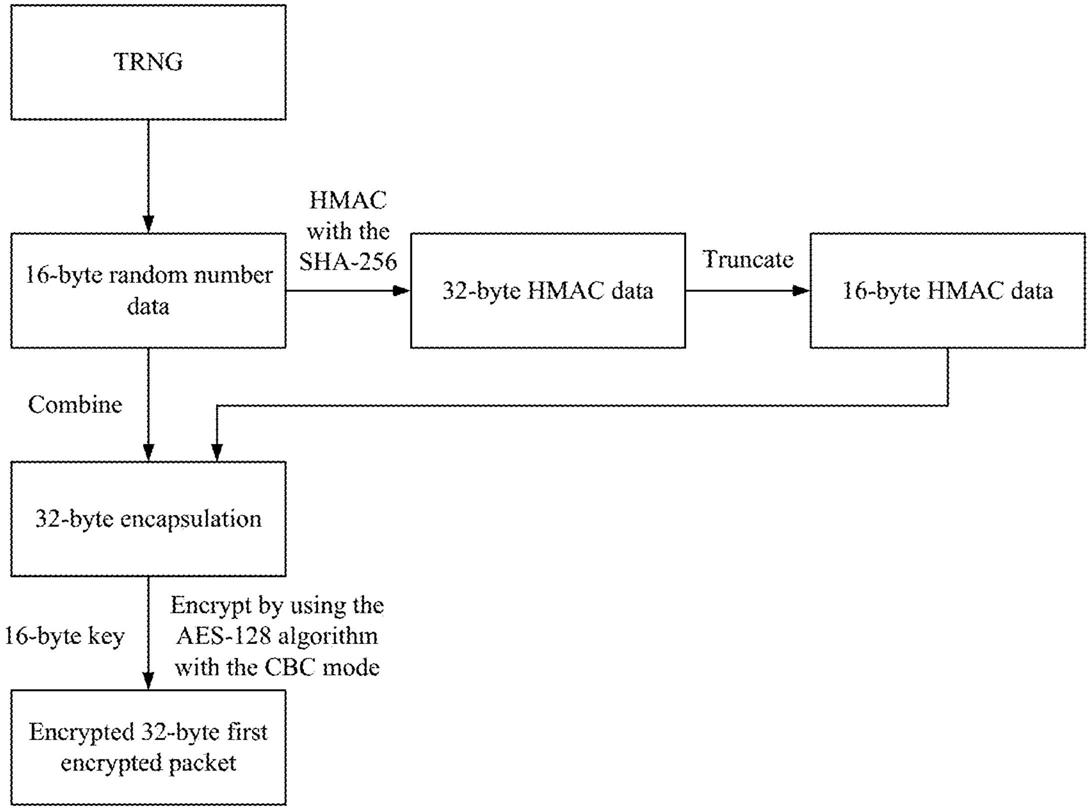
FIG. 3 is a flowchart of generation of a first encrypted packet according to a wireless device authentication method in an embodiment of the present disclosure.
Figure 4:
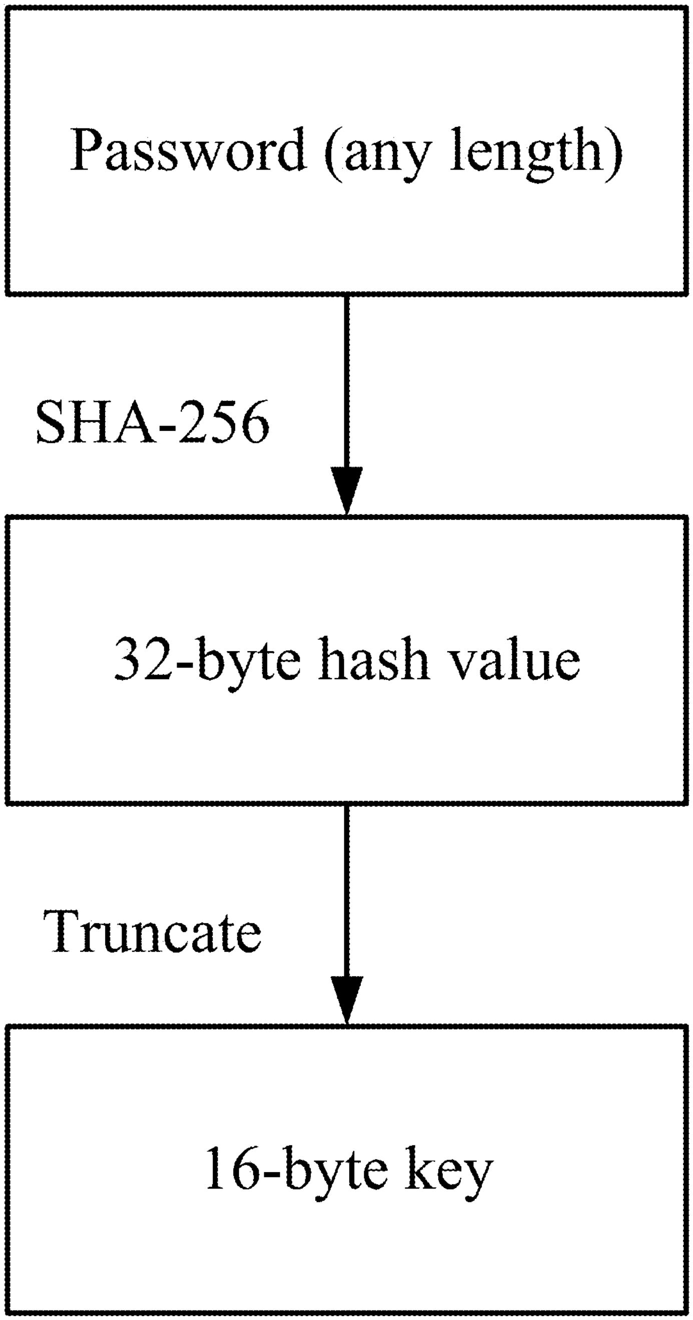
FIG. 4 is a flowchart of generation of a hash-based message authentication code (HMAC) according to a wireless device authentication method in an embodiment of the present disclosure.
Figure 5:
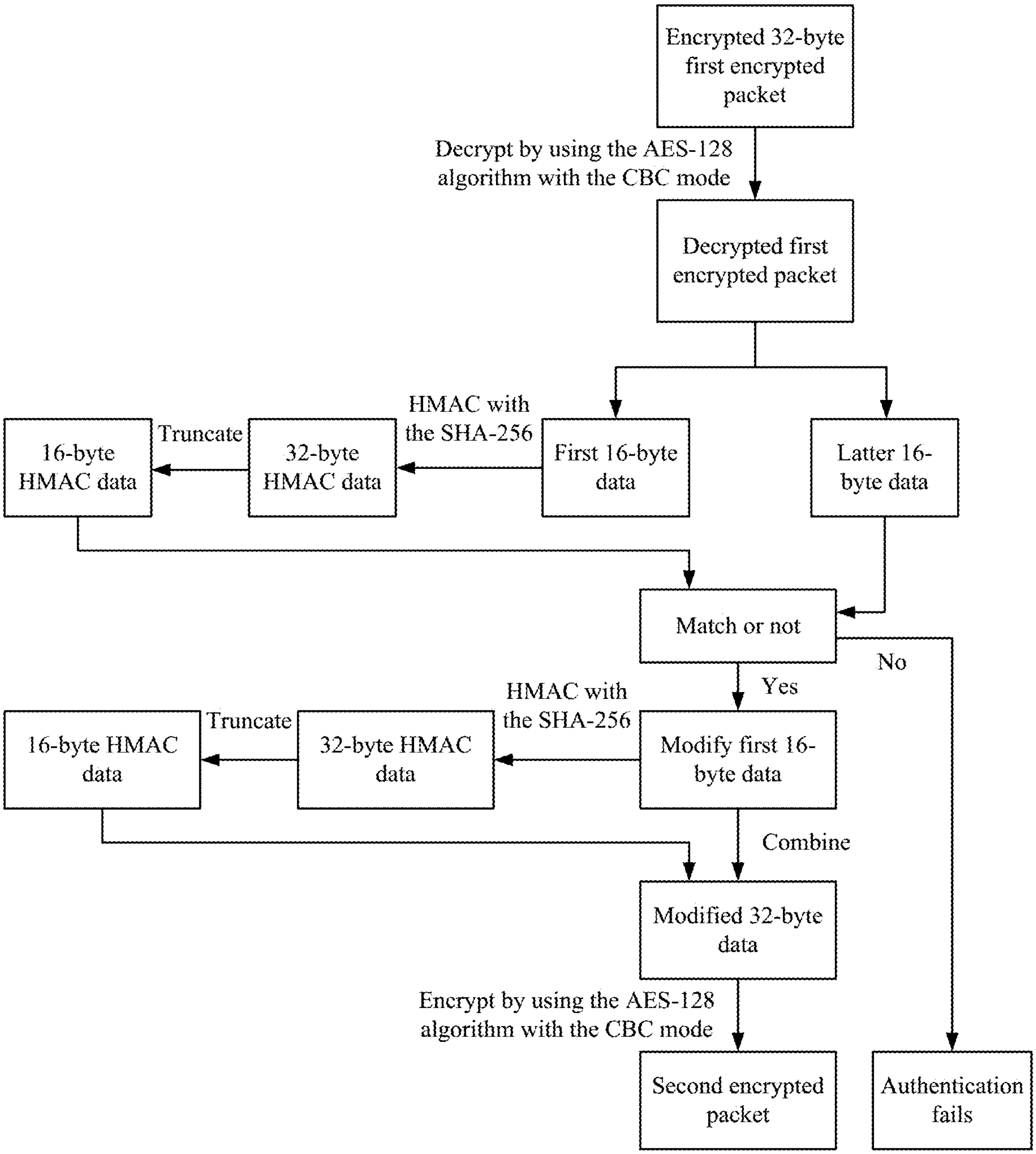
FIG. 5 is a flowchart of generation of a second encrypted packet according to a wireless device authentication method in an embodiment of the present disclosure.
Figure 6:
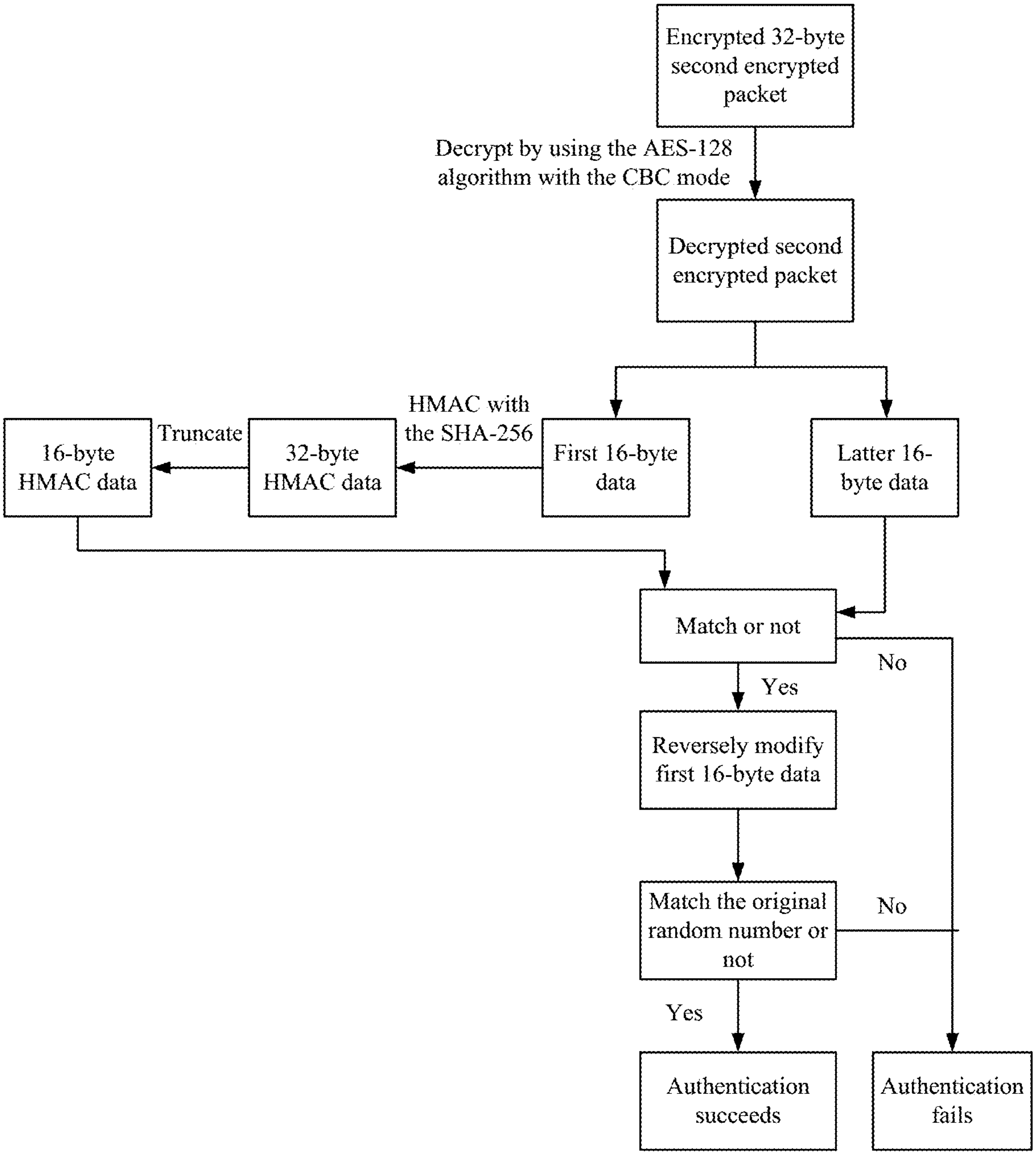
FIG. 6 is a flowchart of authentication of a second encrypted packet according to a wireless device authentication method in an embodiment of the present disclosure.

Please refer to FIGS. 1-6. FIG. 1 is a flowchart of a wireless device authentication method in an embodiment of the present disclosure; FIG. 2 is a flowchart of identity authentication according to a wireless device authentication method in an embodiment of the present disclosure; FIG. 3 is a flowchart of generation of a first encrypted packet according to a wireless device authentication method in an embodiment of the present disclosure; FIG. 4 is a flowchart of generation of a hash-based message authentication code (HMAC) according to a wireless device authentication method in an embodiment of the present disclosure; FIG. 5 is a flowchart of generation of a second encrypted packet according to a wireless device authentication method in an embodiment of the present disclosure; and FIG. 6 is a flowchart of authentication of a second encrypted packet according to a wireless device authentication method in an embodiment of the present disclosure. The wireless device authentication method of the present disclosure will be described in detail below with reference to FIGS. 1-6.

In this embodiment, a wireless device authentication method for a device connected to a target device, includes the following steps:

S101: responding to an authentication request from the target device to generate a first encrypted packet, and sending the first encrypted packet to the target device.

In this embodiment, the device connected to the target device can be a wearable medical device, and the wearable medical device can be used to treat essential tremor. The device provides targeted electrical stimulation to a radial nerve, a median nerve and an ulnar nerve located in a wrist region for the purpose of treatment.

In this embodiment, the target device can be a cloud that controls the device, and a user controls the device's operation through an application program in the cloud. Communication between the cloud and the device can be achieved through Bluetooth, WiFi, 5G, or any other wireless communication mode. A mobile terminal can act as an intermediary for communication between the cloud and the device, and information transmitted by the cloud and the device is forwarded through the mobile terminal, that is, during communication between the cloud and the device, the information between them can be transmitted to each other through the mobile terminal.

In an embodiment, the target device is a cloud, and communication between the cloud and the device is achieved through low-power Bluetooth.

In this embodiment, the step of "responding to an authentication request from the target device to generate a first encrypted packet" includes: receiving the authentication request from target device to generate a random number, and using the random number and a first encryption algorithm corresponding to the key to generate the first encrypted packet.

Optionally, the target device can send an authentication request to the device before the identity authentication (such as a first connection to the device). The device is provided with a true random number generator (TRNG), and the device, after receiving the authentication request, generates a random number through the TRNG.

In this embodiment, the step of "using the random number and a first encryption algorithm corresponding to the key to generate the first encrypted packet" includes: processing the random number using the first encryption algorithm and performing a signature operation using the key to generate a hash-based message authentication code (HMAC); and generating the first encrypted packet according to the HMAC of a pre-set size and the random number. The size of the HMAC can be the same as the random number.

In an embodiment, the first encryption algorithm can be a secure hash algorithm-256 (SHA-256) or any other first encryption algorithm. Both the key and the random number can be composed of 32 bytes, where the key is a 16-byte string. The key is generated from a human-readable password, and the password can consist of numbers and characters of any length. The password is transferred through the SHA-256 algorithm to generate a 32-byte hash value, which is then truncated to generate a final 16-byte key. The TRNG generates a disposable random 16-byte string (a random number). Then, the random number is signed according to the HMAC algorithm with the SHA-256 and also the device's key. 32-byte HMAC data will be generated, and then will be truncated to generate 16-byte data.

In this embodiment, the step of "generating the first encrypted packet according to the HMAC of a pre-set size and the random number" includes: encapsulating the HMAC of the pre-set size and the random number to form a data packet; and encrypting the data packet based on the key and a second encryption algorithm with a preset operating mode to obtain the first encrypted packet, where the preset operating mode includes a cipher block chaining mode.

In this embodiment, the HMAC and the random number are placed at different positions of an encapsulated packet, and the first encryption algorithm and the second encryption algorithm are different encryption algorithms.

In an embodiment, the 16-byte random number data and the 16-byte HMAC data are combined into a 32-byte encapsulated packet. Then, the encapsulated packet is encrypted by using the Advanced Encryption Standard (AES)-128 algorithm with the CBC mode on the basis of the 16-byte key of the device. The final result is a 32-byte first encrypted packet, and the first encrypted packet is transmitted to the target device for authentication of the device by the target device.

S102: receiving the second encrypted packet fed by the target device.

In this embodiment, the second encrypted packet is generated by the target device by modifying the data in the first encrypted packet after verifying the decrypted first encrypted packet. The target device and the device share the key. After the target device receives the first encrypted packet, the first encrypted packet is decrypted based on a pre-stored key, the data in the first encrypted packet passes the authentication, and after determining that the authentication passes (that is, the device passes the authentication of the target device), the data in the first encrypted packet is modified, and the second encrypted packet is generated based on the data of encrypting and modifying the key.

In this embodiment, the authentication of the first encrypted packet is realized by verifying the HMAC by the target device according to the random number and the pre-stored key.

The target device pre-stores information about the encryption algorithm corresponding to the first encrypted packet, and decrypts the first encrypted packet based on the encryption algorithm and the key. Further, after decrypting the first encrypted packet, the target device obtains the random number and the HMAC in the first encrypted packet. The random number is processed based on a generation method of the HMAC to obtain a new HMAC. When the new HMAC matches the HMAC in the first encrypted packet, it is determined that the authentication passes.

In an embodiment, the target device decrypts the packet in the CBC mode by using the 16-byte key and the AES-128 algorithm. The decrypted first encrypted packet is divided into two parts of data: 16-byte data (first) and 16-byte data (latter). Then, the first 16-byte data is fed through the HMAC algorithm of the SHA-256 and signed with the key of an application. Then, the 32-byte HMAC result is truncated to generate 16-byte data. Then, the application checks whether the 16-byte HMAC data matches the latter 16-byte data in the first encrypted packet. When determining that they match, packet integrity passes the authentication, and the application knows that its key matches the device's key; and otherwise, the identity authentication fails.

In this embodiment, after determining that the authentication of the first encrypted packet passes, the target device modifies the random number in the first encrypted packet, and generates a new HMAC according to the modified random number. The modified random number and the HMAC corresponding to the random number are encrypted with the same encryption manner for the first encrypted packet to obtain the second encrypted packet.

In an embodiment, the target device modifies the random number of the first 16-byte data in the first encrypted packet. This can be implemented in various ways, and in an embodiment, all bits of the random number are flipped. Then, the modified 16-byte data is fed through the HMAC algorithm, signed with the key of the application, and truncated to generate new 16-byte data. Then, the modified 16-byte data and corresponding HMAC data are combined to generate a new modified 32-byte packet. Then, this packet is encrypted with the AES-128 algorithm and the key stored in the target device. Then, the modified and encrypted 32-byte second encrypted packet is transmitted back to the device.

S103: when the second encrypted packet meets pre-set conditions, determining that the target device has passed authentication, and responding to an encrypted instruction sent by the target device.

In this embodiment, the pre-set conditions include that the keys corresponding to the second encrypted packet and the first encrypted packet are the same and the second encrypted packet has passed integrity authentication.

In this embodiment, the second encrypted packet includes first data and second data, where the first data includes the random number generated after modifying in a pre-set manner, and the second data includes the HMAC corresponding to the modified random number; steps before the integrity authentication of the second encrypted packet include: decrypting the second encrypted packet using the key corresponding to the first encrypted packet to obtain the first data and the second data in the second encrypted packet; and obtaining the HMAC corresponding to the first data according to the first encryption algorithm and the key, and when determining that a pre-set part of the HMAC matches the second data, performing the integrity authentication of the second encrypted packet.

In this embodiment, the random number in the second encrypted packet is modified based on the random number modification method for the target device to obtain a random number (i.e., the random number in the first encrypted packet) before the target device is modified. Specifically, the integrity authentication of the second encrypted packet includes: changing the first data according to the pre-set manner to obtain third data; and when determining that the third data matches the random number in the first encrypted packet, determining that the integrity authentication passes.

In an embodiment, the device decrypts the second encrypted packet using the key corresponding to the first encrypted packet. The decrypted packet is divided into two parts of data: 16-byte data (first) and 16-byte data (latter). Then, the first 16-byte data is fed through the HMAC algorithm of the SHA-256 and signed with the device's key. Then, the 32-byte HMAC result is truncated to generate 16-byte data. Then, the device checks whether the 16-byte HMAC data matches the latter 16-byte data in the second encrypted packet. When determining that they match, packet integrity passes the authentication, and otherwise, the identity authentication fails. Next, the device reversely modifies the first 16-byte data according to the modification method of the target device. For example, the target device modifies the data by flipping all bits, and then all the bits are flipped back for modification of the device. The device checks whether the modified result matches an original random number in the first encrypted packet. When they match, the identity authentication succeeds, and when determining that the target device has passed the identity authentication, a control instruction sent by the target device is executed. Otherwise, the identity authentication fails.

In this embodiment, before sending an authentication request to the device, the target device checks whether it is connected to the device for the first time. When determining the first connection with the device, a pre-set password is used to verify a user of the device; and when determining that the authentication fails, it is prompted that the current connection is illegal, and connection with the device is refused; and when determining that the authentication succeeds, a new password inputted by the user is obtained, and the preset password is replaced with the new password. The preset password is a public password, and password leakage can be avoided through password replacement.

In this embodiment, when the target device or the device determines that the second encrypted packet passes integrity authentication, a new key is generated, the encrypted key is transferred to the device or the target device in an encryption manner for the first encrypted packet or the second encrypted packet, and a configuration file of the user corresponding to the device is stored.

In an embodiment, when the target device is connected to a new device for the first time, a default password will be used to verify the identity of the user. When the authentication with the default password fails, the target device prompts that the current connection is illegal, and refuses data transmission with the new device. When determining that the authentication succeeds, the user is required to enter a new password. The preset password is replaced with the new password, and the new password is used to authenticate corresponding users of any other devices connected to the target device for the first time to ensure that the target device will not be illegally connected next time. The target device and the connected new device are authenticated by use of the first encrypted packet and the second encrypted packet. After determining that the second encrypted packet has passed integrity authentication, the target device will automatically generate a new 16-byte key. The new key is transmitted to the device for authentication through the same encryption scheme mentioned above. After determining that the authentication succeeds, the target device and the new device replace the old key with the new 16-byte key. The new key is stored in the device's flash memory, and an associated user's configuration file can be stored on the target device and a cloud server related to the target device.

In this embodiment, to solve the problem that the user forgets the password, when the target device determines that the user satisfies the pre-set conditions and operates the device in the pre-set manner, the current password is set as the pre-set password, where the pre-set conditions include that the user has the authority of physical access to the device.

In an embodiment, when the user forgets the password, the user can perform a specific button sequence operation (i.e., inputting the fault information indicating the fact of forgetting the password) on the device to reset the password to a default value. This ensures that anyone with permissions of physical access to the device can use the device. For example, the button sequence operation may involve the following steps: (1) turning on the device in an idle mode, (2) pressing an UP button once, (3) pressing a DOWN button once, (4) holding down a MIDDLE button (a button between the UP button and the DOWN button) for about 3 sec to turn off the device, where the device receives the information generated by the above operation, determines that the user has forgotten the password, and controls all LED lights to flash transiently to confirm a correct sequence.

The wireless device authentication method of the present disclosure can prevent data leakage, and even though the communication is eavesdropped, the transmitted content is encrypted through the AES-128 algorithm with the CBC mode. Further, for each identity authentication, a new disposable random number is generated. The probability of generating the same random number twice is negligible. An attacker may send a false data packet to the application or the device. However, without the key, a data integrity test will fail, so the application or the device will not respond to the attacker's instructions, thereby reducing the possibility of unauthorized use of the device.

Beneficial effects: the wireless device authentication method of the present disclosure includes: responding to an authentication request from the target device to generate a first encrypted packet, and sending the first encrypted packet to the target device; receiving a second encrypted packet generated by the target device by modifying the data in the first encrypted packet after verifying the decrypted first encrypted packet passes authentication; and determining that the target device has passed identity authentication when the second encrypted packet meets pre-set conditions, and responding to an encrypted instruction sent by the target device. The present disclosure, during communication with the target device, is capable of device authentication by means of the first encrypted packet and the second encrypted packet generated with the same key, thereby improving communication security, avoiding data leakage and unauthorized use of a device, and reducing the risk of remote control of the device.

Figure 7:
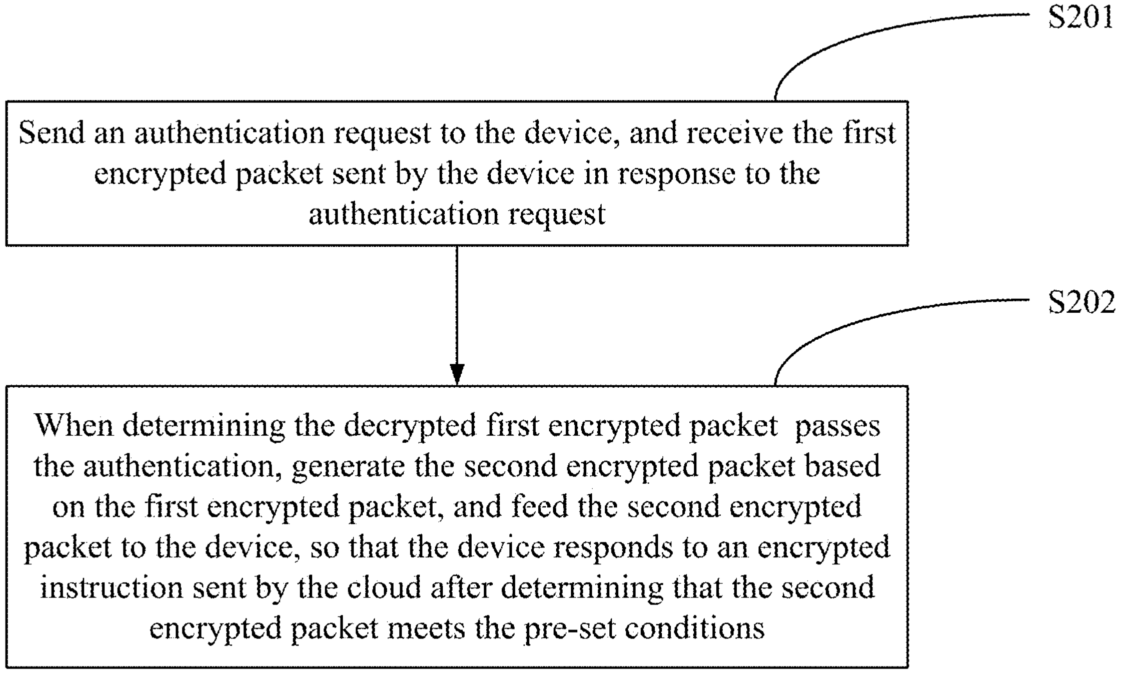
FIG. 7 is a flowchart of a wireless device authentication method in another embodiment of the present disclosure.

Based on the same inventive concept, the present disclosure further provides a wireless device authentication method for a cloud connected to a device, where a cloud application sends the authentication request and feeds the second encrypted packet, and as shown in FIG. 7, the wireless device authentication method includes the following steps:

S201: sending an authentication request to the device, and receiving the first encrypted packet sent by the device in response to the authentication request.

S202: when determining that the decrypted first encrypted packet passes the authentication, generating the second encrypted packet based on the first encrypted packet, and feeding the second encrypted packet to the device, so that the device responds to an encrypted instruction sent by the cloud after determining that the second encrypted packet meets the pre-set conditions.

In this embodiment, the pre-set conditions include that the keys corresponding to the second encrypted packet and the first encrypted packet are the same and the second encrypted packet has passed integrity authentication.

In this embodiment, steps before sending the authentication request to the device include: when determining a first connection with the device, using a pre-set password to verify a user of the device; when determining that the authentication fails, prompting that the current connection is illegal; when determining that the authentication succeeds, obtaining a new password inputted by the user and replacing the preset password with the new password; and using the new password to authenticate corresponding users of any other devices connected to the target device for the first time to ensure that the cloud will not be illegally connected next time.

In this embodiment, the method further includes: when determining that the authentication passes, generating a new key, transferring the encrypted key to the device in an encryption manner for the first encrypted packet or the second encrypted packet, and storing a configuration file of the user corresponding to the device.

In this embodiment, the method further includes: when determining that the user satisfies the pre-set conditions and operates the device in the pre-set manner, setting the current password as the pre-set password, where the pre-set conditions include that the user has the authority of physical access to the device.

In this embodiment, the step of "the device responds to an authentication request from the cloud to generate a first encrypted packet" includes: receiving the authentication request from cloud to generate a random number, and using the random number and a first encryption algorithm corresponding to the key to generate the first encrypted packet.

In this embodiment, the step of "using the random number and a first encryption algorithm corresponding to the key to generate the first encrypted packet" includes: processing the random number using the first encryption algorithm and performing a signature operation using the key to generate a hash-based message authentication code (HMAC); and generating the first encrypted packet according to the HMAC of a pre-set size and the random number.

In this embodiment, the step of "generating the first encrypted packet according to the HMAC of a pre-set size and the random number" includes: encapsulating the HMAC of the pre-set size and the random number to form a data packet; and encrypting the data packet based on the key and a second encryption algorithm with a preset operating mode to obtain the first encrypted packet, where the preset operating mode includes a cipher block chaining (CBC) mode.

In this embodiment, the authentication of the first encrypted packet is realized by verifying the HMAC by the target device according to the random number and the pre-stored key.

In this embodiment, the second encrypted packet that meets the pre-set conditions includes first data and second data, where the first data includes the random number generated after modifying in a pre-set manner, and the second data includes the HMAC corresponding to the modified random number; steps before the integrity authentication of the second encrypted packet include: decrypting the second encrypted packet using the key corresponding to the first encrypted packet to obtain the first data and the second data in the second encrypted packet; and obtaining the HMAC corresponding to the first data according to the first encryption algorithm and the key, and when determining that a pre-set part of the HMAC matches the second data, performing the integrity authentication of the second encrypted packet.

In this embodiment, the integrity authentication of the second encrypted packet includes: changing the first data according to the pre-set manner to obtain third data; and when determining that the third data matches the random number in the first encrypted packet, determining that the integrity authentication passes.

Figure 8:
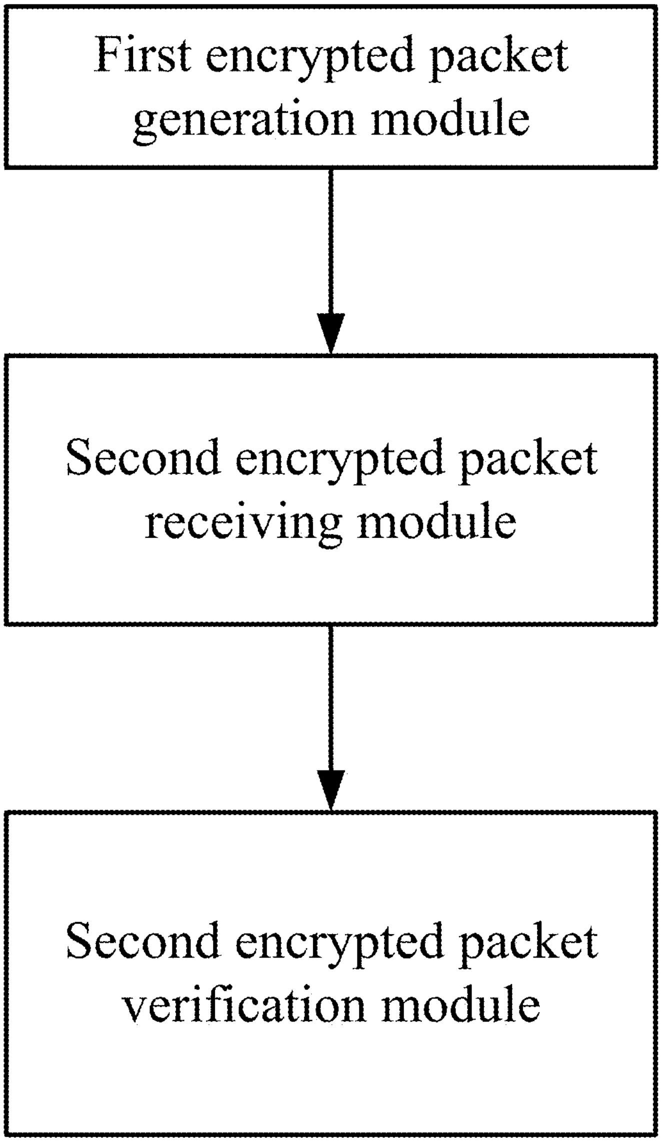
FIG. 8 is a structural schematic diagram of a wearable medical device according to an embodiment of the present application.

Based on the same inventive concept, the present disclosure further provides a wearable medical device. As shown in FIG. 8, the wearable medical device includes a first encrypted packet generation module, a second encrypted packet receiving module, and a second encrypted packet authentication module. The first encrypted packet generation module is configured for responding to an authentication request from the target device to generate a first encrypted packet, and sending the first encrypted packet to the target device, where the target device includes a cloud that controls the wearable medical device; the second encrypted packet receiving module is configured for receiving a second encrypted packet generated by the target device by modifying the data in the first encrypted packet after verifying the decrypted first encrypted packet passes authentication; and the second encrypted packet authentication module is configured for determining that the target device has passed authentication when the second encrypted packet meets pre-set conditions, and responding to an encrypted instruction sent by the target device. The pre-set conditions include that the keys corresponding to the second encrypted packet and the first encrypted packet are the same and the second encrypted packet has passed integrity authentication.

Figure 9:
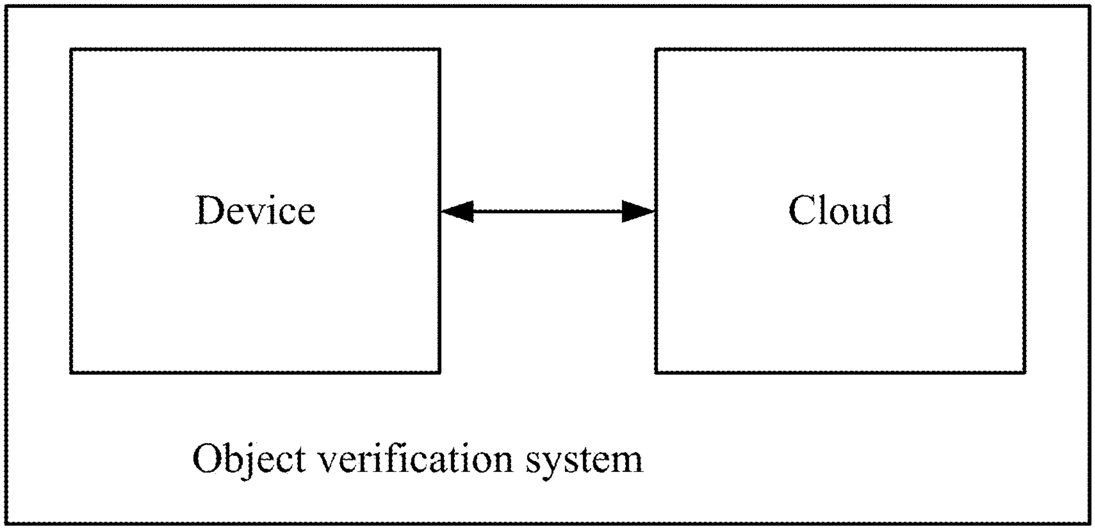
FIG. 9 is a structural schematic diagram of a device authentication system in an embodiment of the present disclosure.

Based on the same inventive concept, the present disclosure further provides a device authentication system. As shown in FIG. 9, the device authentication system includes a device and a cloud, where the cloud is in communication connection with the device, and the device authentication system implements the wireless device authentication method described in the above embodiments through the cloud and the device. The device and the cloud mutually verify each other through the wireless device authentication method to ensure that information is transmitted only between authorized devices.

In this embodiment, the device authentication system may further include a mobile terminal, the mobile terminal can be connected to both the cloud and the device, and the device can interact with the mobile terminal for data exchange. To prevent data leakage, the mobile terminal will only forward the data instead of processing the data. The device can also verify the mobile terminal when it is connected to the mobile terminal, and after determining that the mobile terminal passes the authentication (the password entered by the mobile terminal is the default password or an identification code of the mobile terminal matches the identification code recorded in the device), the device will exchange data with the cloud through the mobile terminal.

In an embodiment of the present disclosure, there is further provided a computer product, including a computer program, where when the computer program is executed by the processor, the steps of any method provided by the present disclosure are implemented or the steps of various optional implementations of the method provided by the present disclosure are implemented.

Each embodiment in the description is described in a progressive manner, each embodiment focuses on the differences from other embodiments, and the same and similar parts between the embodiments may refer to each other.

The above description of the disclosed embodiments enables any person skilled in the art to implement or use the present disclosure. Various modifications to these embodiments will be readily apparent to those skilled in the art, and the generic principles defined herein may be implemented in other embodiments without departing from the spirit or scope of the present disclosure. Thus, the present disclosure is not intended to be limited to the embodiments shown herein, but is to be accorded with the widest scope consistent with the principles and novel features disclosed herein.

What it claimed is:

1. A wireless device authentication method for a device connected to a target device, comprising the following steps:

responding to an authentication request from the target device to generate a first encrypted packet, and sending the first encrypted packet to the target device, wherein the target device includes a cloud that controls the device;

receiving a second encrypted packet fed by the target device, wherein the second encrypted packet is generated by the target device by modifying the data in the first encrypted packet after verifying the decrypted first encrypted packet passes authentication; and when the second encrypted packet meets pre-set conditions, determining that the target device has passed authentication, and responding to an encrypted instruction sent by the target device, wherein the pre-set conditions include that the keys corresponding to the second encrypted packet and the first encrypted packet are the same and the second encrypted packet has passed integrity authentication;

wherein the step of "responding to an authentication request from the target device to generate a first encrypted packet" comprises: receiving the authentication request from the target device to generate a random number, and using the random number and a first encryption algorithm corresponding to the key to generate the first encrypted packet;

the step of "using the random number and a first encryption algorithm corresponding to the key to generate the first encrypted packet" comprises: processing the random number using the first encryption algorithm and performing a signature operation using the key to generate a hash-based message authentication code (HMAC); and generating the first encrypted packet according to the HMAC of a pre-set size and the random number;

wherein the step of "generating the first encrypted packet according to the HMAC of a pre-set size and the random number" comprises: encapsulating the HMAC of the pre-set size and the random number to form a data packet; and encrypting the data packet based on the key and a second encryption algorithm with a preset operating mode to obtain the first encrypted packet, wherein the preset operating mode comprises a cipher block chaining mode.

2. The wireless device authentication method according to claim 1, wherein the authentication of the first encrypted packet is realized by verifying the HMAC by the target device according to the random number and the pre-stored key.

3. The wireless device authentication method according to claim 1, wherein the second encrypted packet that meets the pre-set conditions comprises first data and second data, wherein the first data comprises the random number generated after modifying in a pre-set manner, and the second data comprises the HMAC corresponding to the modified random number;

steps before the integrity authentication of the second encrypted packet comprise:

decrypting the second encrypted packet using the key corresponding to the first encrypted packet to obtain the first data and the second data in the second encrypted packet; and obtaining the HMAC corresponding to the first data according to the first encryption algorithm and the key, and when determining that a pre-set part of the HMAC matches the second data, performing the integrity authentication of the second encrypted packet.

4. The wireless device authentication method according to claim 1, wherein the integrity authentication of the second encrypted packet comprises:

changing the first data according to the pre-set manner to obtain third data; and when determining that the third data matches the random number in the first encrypted packet, determining that the integrity authentication passes.

5. A wireless device authentication method for a cloud connected to a device, comprising the following steps:

sending an authentication request to the device, and receiving the first encrypted packet sent by the device in response to the authentication request; and when determining that the decrypted first encrypted packet passes the authentication, generating the second encrypted packet based on the first encrypted packet, and feeding the second encrypted packet to the device, so that the device responds to an encrypted instruction sent by the cloud after determining that the second encrypted packet meets the pre-set conditions, wherein the pre-set conditions comprise that the keys corresponding to the second encrypted packet and the first encrypted packet are the same and the second encrypted packet has passed the integrity authentication, wherein generating the second encrypted packet comprises performing a bit-flip operation on a random number contained within the first encrypted packet.

6. The wireless device authentication method according to claim 5, wherein steps before sending the authentication request to the device comprise:

when determining a first connection with the device, using a pre-set password to verify a user of the device;

when determining that the authentication fails, prompting that the current connection is illegal; and when determining that the authentication succeeds, obtaining a new password inputted by the user and replacing the preset password with the new password.

7. The wireless device authentication method according to claim 5, further comprising:

when determining that the authentication passes, generating a new key, transferring the encrypted key to the device in an encryption manner for the first encrypted packet or the second encrypted packet, and storing a configuration file of the user corresponding to the device.

8. The wireless device authentication method according to claim 6, further comprising:

when determining that the user satisfies the pre-set conditions and operates the device in the pre-set manner, setting the current password as the pre-set password, wherein the pre-set conditions comprise that the user has the authority of physical access to the device.

9. A wearable medical device, comprising:

a first encrypted packet generation module, being configured for responding to an authentication request from the target device to generate a first encrypted packet, and sending the first encrypted packet to the target device, wherein the target device comprises a cloud that controls the wearable medical device;

a second encrypted packet receiving module, being configured for receiving a second encrypted packet fed by the target device, wherein the second encrypted packet is generated by the target device by modifying the data in the first encrypted packet after verifying the decrypted first encrypted packet passes authentication; and a second encrypted packet authentication module, being configured for determining that the target device has passed authentication when the second encrypted packet meets pre-set conditions, and responding to an encrypted instruction sent by the target device, wherein the pre-set conditions include that the keys corresponding to the second encrypted packet and the first encrypted packet are the same and the second encrypted packet has passed integrity authentication, wherein the step of “responding to an authentication request from the target device to generate a first encrypted packet” comprises: receiving the authentication request from the target device to generate a random number, and using the random number and a first encryption algorithm corresponding to the key to generate the first encrypted packet;

the step of “using the random number and a first encryption algorithm corresponding to the key to generate the first encrypted packet” comprises: processing the random number using the first encryption algorithm and performing a signature operation using the key to generate a hash-based message authentication code (HMAC); and generating the first encrypted packet according to the HMAC of a pre-set size and the random number;

wherein the step of “generating the first encrypted packet according to the HMAC of a pre-set size and the random number” comprises: encapsulating the HMAC of the pre-set size and the random number to form a data packet; and encrypting the data packet based on the key and a second encryption algorithm with a preset operating mode to obtain the first encrypted packet, wherein the preset operating mode comprises a cipher block chaining mode.

10. A device authentication system, comprising a device and a cloud, wherein the cloud is in communication connection with the device, and the device authentication system implements the method according to claim 1 through the cloud and the device.

11. A computer product, comprising a computer program, wherein when the computer program is executed by the processor, the steps of the method according to claim 1 are implemented.

* * * * *